(12) United States Patent
Grund et al.

(10) Patent No.: US 6,217,519 B1
(45) Date of Patent: Apr. 17, 2001

(54) DEVICE AND METHOD FOR OBSERVING VESSELS, SPECIALLY BLOOD VESSELS

(75) Inventors: Karl-Ernst Grund, Tübingen; Martin Kimmel, Esslingen; Dieter Denner, Sipplingen; Gerold Widenhorn, Überlingen; Jürgen Zolondz, Radolfzell, all of (DE)

(73) Assignee: DWL Elektronische Systeme GmbH (DE)

( * ) Notice: Subject to any disclaimer, the term of this patent is extended or adjusted under 35 U.S.C. 154(b) by 0 days.

(21) Appl. No.: 09/194,174

(22) PCT Filed: Mar. 24, 1998

(86) PCT No.: PCT/EP98/01733

§ 371 Date: Nov. 20, 1998

§ 102(e) Date: Nov. 20, 1998

(87) PCT Pub. No.: WO98/42259

PCT Pub. Date: Oct. 1, 1998

(30) Foreign Application Priority Data

Mar. 25, 1997 (DE) ............................................. 197 12 572
Jan. 23, 1998 (DE) ............................................. 198 02 474

(51) Int. Cl.[7] ........................................................ A61B 8/12
(52) U.S. Cl. ............................................................ 600/463
(58) Field of Search .................................. 600/437, 440, 600/441, 443, 447, 462–463, 466–467, 471, 109, 168

(56) References Cited

U.S. PATENT DOCUMENTS 4,582,067   4/1986  Silverstein et al. .
5,054,491  10/1991  Saito et al. .
5,178,150 *  1/1993  Silverstein et al. .................. 600/463
5,394,878   3/1995  Frazin et al. .
5,588,434 * 12/1996  Fujimoto ............................. 600/443
5,680,865 * 10/1997  Tanaka ................................ 600/441

FOREIGN PATENT DOCUMENTS 39 34 644 A1   4/1990  (DE) .
38 38 396 A1   5/1990  (DE) .
0 668 052 A2   8/1995  (EP) .

* cited by examiner

*Primary Examiner*—Francis J. Jaworski
(74) *Attorney, Agent, or Firm*—Piper Marbury Rudnick & Wolfe

(57) ABSTRACT

The invention concerns an apparatus for viewing vessels, in particular blood vessels, in body cavities and hollow organs, comprising an ultrasonic transducer (14) which can be guided into a viewing position by means of an endoscopy device (10, 12), an ultrasonic unit (34) which can be connected to the ultrasonic transducer (14) and which is based on the Doppler principle and which is designed to detect an organ and/or fluid movement at at least one predetermined spacing from the ultrasonic transducer, a Doppler evaluation unit (38) which is connected downstream of the ultrasonic unit (34) and which is designed for digital conversion of an output signal of the ultrasonic unit (34) into a visual representation of the organ and/or fluid movement at the at least one predetermined spacing, and a video output unit (40) which receives an output image signal of the Doppler evaluation unit (38) and an electronic image signal of the endoscopy device (12) and which is designed to produce a combined overall image (24) for a display screen which can show both an endoscopy image (26) and also at least one representation (28) of the organ and/or fluid movement.

17 Claims, 4 Drawing Sheets

DEVICE AND METHOD FOR OBSERVING VESSELS, SPECIALLY BLOOD VESSELS

DESCRIPTION

Figure 1:
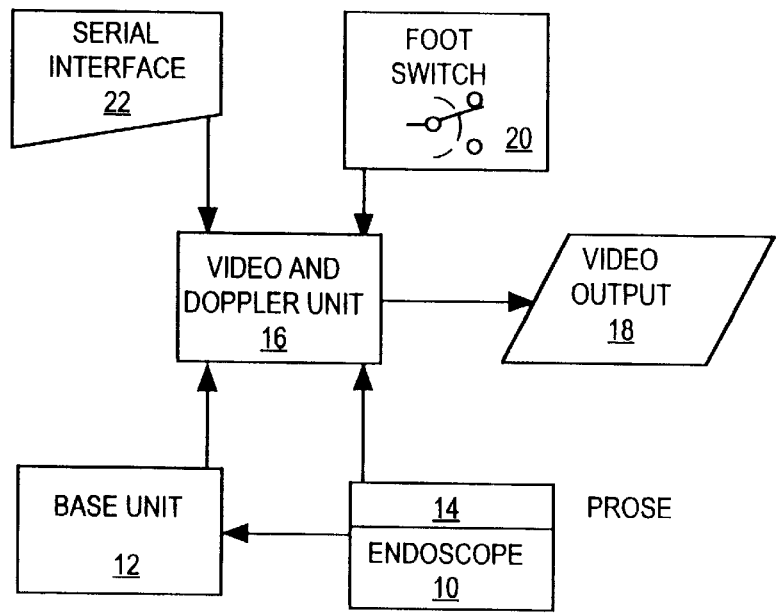

The present invention concerns an apparatus and a process for viewing vessels, in particular blood vessels, on the body, in body cavities and hollow organs.

It is known from the state of the art, for the purposes of inspecting body cavities or hollow organs in the interior of the body, for example the stomach or the intestinal tract, to introduce an endoscope in order to obtain a visual impression of a condition to be diagnosed in the respective region of the body, by virtue of the image representation afforded by the endoscope. The technology, structure and mode of operation of endoscopes of that kind are known, in which respect in particular the more modern endoscopes have an endoscope conduit which is afforded by means of optical fibers, for being inserted into the body, and the image which is produced in that way is detected by way of an electronic image sensor and electronically processed for display on a (video) screen. There are also endoscopes which have the image sensor (for example a CCD) at the operational insertion end.

Performing endoscopy in a practical context however frequently involves the problem that (blood) vessels are present at locations, for example an ulcer or sore, which are specifically relevant for diagnosis or treatment, and such vessels require particular attention or extreme care when carrying out interventions or when performing a targeted treatment in order to reduce the risk of bleeding. As moreover blood vessels of that kind are surrounded by tissue or organ walls of the respective body cavity being viewed, they are generally not visually perceptible by purely endoscopic inspection.

It is admittedly also known from the state of the art to use ultrasound sonography procedures generally for investigating blood flows and thus also for the detection of blood vessels, but this involves quite serious difficulties in particular when working in the interior of the body, and for that reason it has hitherto not been possible to implement it in terms of clinical practice.

Therefore the object of the present invention is to add to apparatuses or procedures in endoscopy or, generally, visual viewing of body cavities or hollow organs, a function which makes it possible to detect blood vessels—which are usually concealed or invisible—at the viewing or intervention location. In that respect, the invention seeks to provide both a suitable viewing apparatus and also an associated working or operational process.

That object is attained by the apparatus as set forth in claim 1 and the process as set forth in claim 17.

Advantageously in that respect the provision of an ultrasonic probe for a (preferably multi-channel) Doppler ultrasonic evaluation at the intervention end of the carrier which is preferably in the form of an endoscope conduit or guide permits simultaneous monitoring for (blood) vessels and the production of suitable, flow-dependent image information in regard to viewing the detected image, and the video output unit which is provided in accordance with the invention allows simultaneous visual monitoring of those procedures with a single glance at a common output display screen.

Accordingly, viewing and treatment of two diagnostically interrelated situations is permitted and promoted in a manner which is significant in terms of clinical practice, without a plurality of items of equipment having to be simultaneously operated and viewed, and without attention being distracted by virtue of additional attention having to be paid to operation of the equipment.

Admittedly, it is preferable in accordance with the invention for it to be used in conjunction with an endoscopy device in which it is also used as a carrier device for the ultrasonic transducer; the invention however is not limited to that embodiment. It is thus generally in accordance with the invention to use any electrical image pick-up device on a suitable carrier, together with the ultrasonic transducer. For example the invention is also suitable for use in conjunction with an operational microscope in which the image detection element, for transmission of the microscope image, is associated with the microscope optical system while, at the intervention end, the ultrasonic transducer can be carried on the microscope (or is disposed externally thereof); in that respect the microscope acts as the carrier device according to the invention.

Further regions of use which go therebeyond would then be for example laparoscopy or neurosurgery. In general therefore the invention extends to correspondingly associated video or graphics sources.

The arrangement of the ultrasonic transducer on the carrier device is admittedly also particularly preferred; nonetheless however the invention also embraces a construction in which the ultrasonic transducer can be guided independently and separately from the image element or an associated carrier, for example by way of a hand-held probe. That configuration would also be possible for example with an operational or video microscope.

Advantageous developments of the invention are described in the appendant claims.

Thus in particular the multi-channel resolution, which is graduated or staggered in respect of depth, of ultrasonic Doppler monitoring, permits depth detection of a respective blood vessel, and that is extremely useful in a practical context. More specifically, it is precisely in implementing possible operative interventions that it has been found important to be certain in advance whether there is a blood vessel present and if so, at what depth such a blood vessel is to be found.

It is precisely by virtue of the combination according to the invention of the Doppler probe with an endoscope tip which establishes the viewing plane for the visual endoscopy image that the ultrasonic probe is in a fixedly defined position and thus permits reliable imaging of the possible (blood) flow conditions in the organ tissue or the wall relative to the endoscope head.

Advantageously, the invention also permits switching over as required between a pure endoscopy representation and a mixed or hybrid representation which is specified in the manner according to the invention, in particular for the situation where a vessel is assumed to occur at an intervention position which is considered to be particularly relevant.

In accordance with a further development of the invention, the video output unit is also based on a digital video mixer. That can then not only provide in a simple manner for simple processing of the Doppler image—which is in any case digital by virtue of the evaluation or computation procedure involved—; in addition, this also permits simple adaptation as required of the endoscope image, for example with the scaling unit which is to be provided in accordance with the development of the invention for a reduction or increase in size respectively.

The apparatus according to the invention is further advantageous for the supply or output of image signals of a plurality of different current image standards, in particular TV-picture standards. In that respect, in accordance with the development of the invention, image signals can be outputted in particular also in parallel, that is to say simultaneously, using different standards.

In accordance with a further preferred embodiment of the invention it is also possible for the ultrasonic transducer itself, that is to say the probe head, to be changed in regard to its position at the intervention end of the carrier (for example of the endoscope tube). That advantageously provides for signal optimisation or adaptation to respectively specific viewing circumstances.

It is advantageously also in accordance with the invention to arrange for the probe head to rotate and/or to fit a lens for varying the sound field or to make the probe head movable in the form of a controllable probe.

Overall therefore the invention affords completely new options in regard to for example endoscope-aided (or generally: micro-invasive) exploration, diagnosis and therapy. Now, for the first time, an operator is enabled in one glance to effect an endoscopic investigation and at the same time to carry out a check for (concealed) blood vessels at locations which run a potential risk of bleeding, without for example further (expensive) procedures or operating steps being required.

Figure 2:
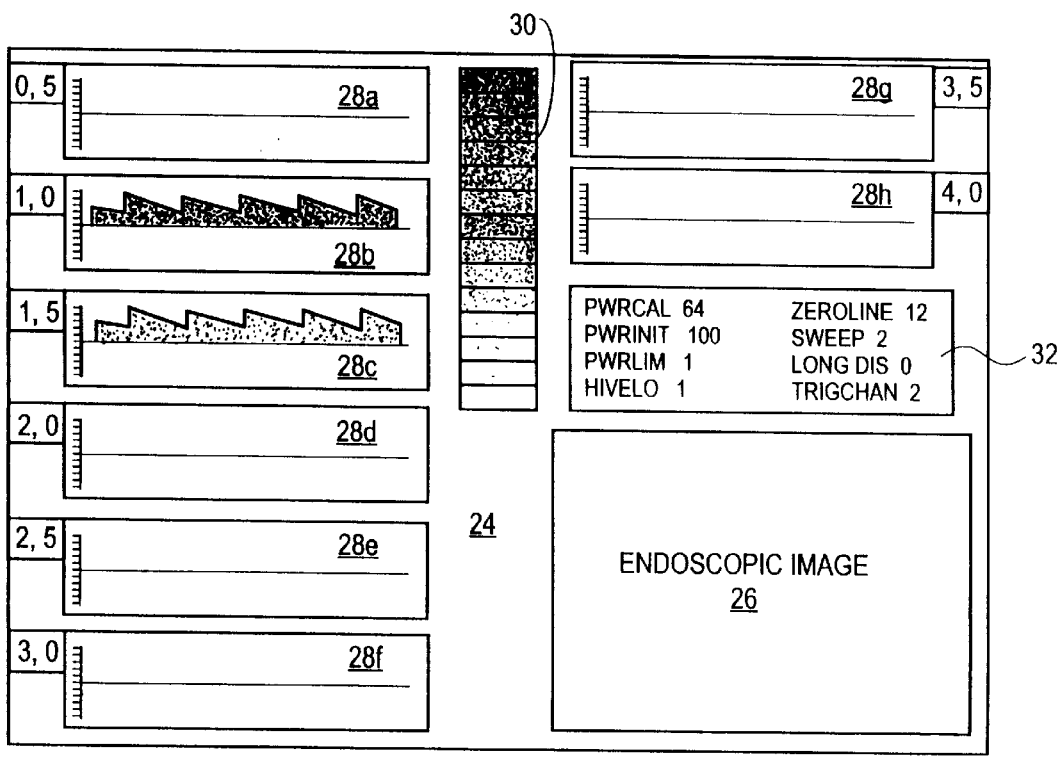
Figure 3:
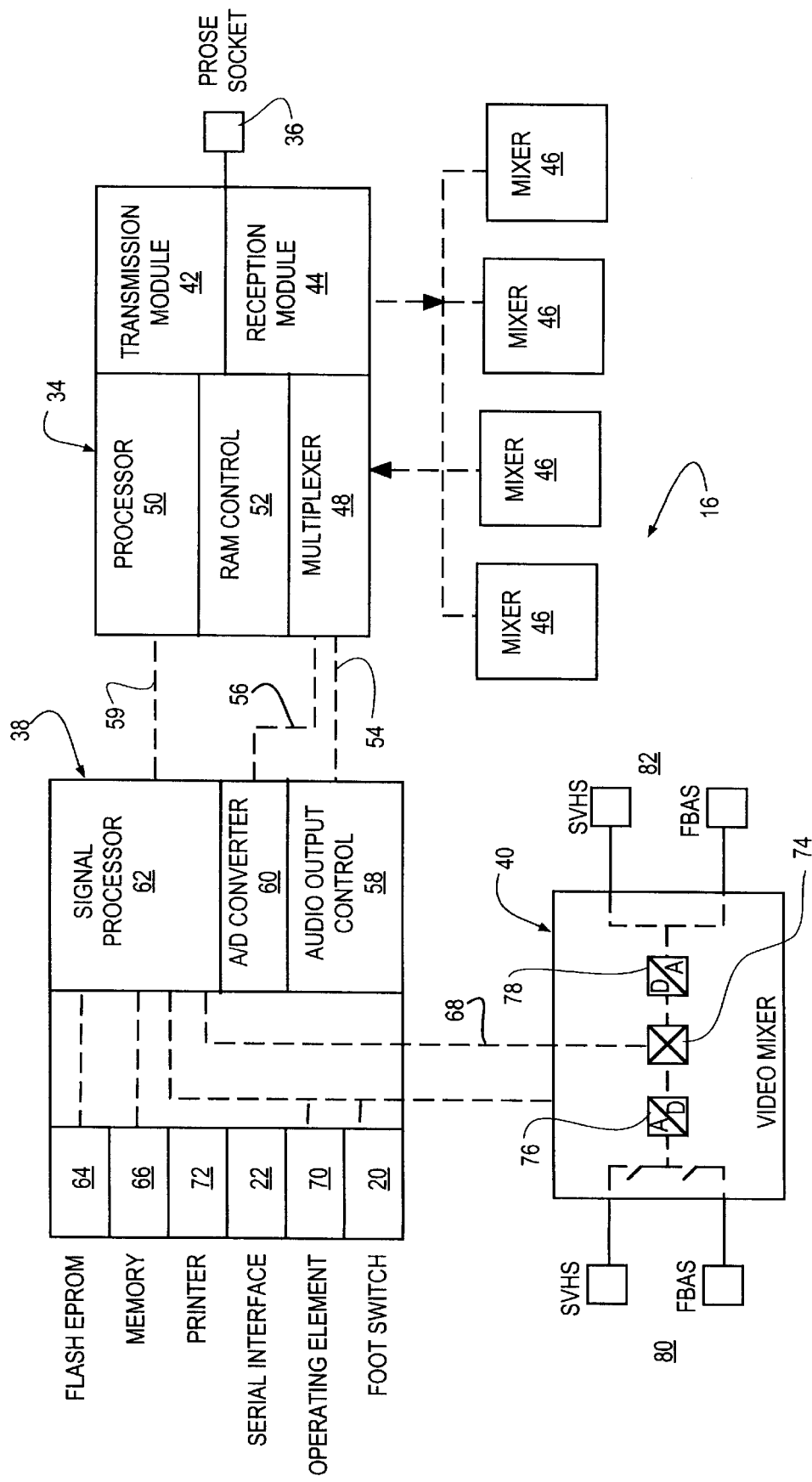
Figure 4:
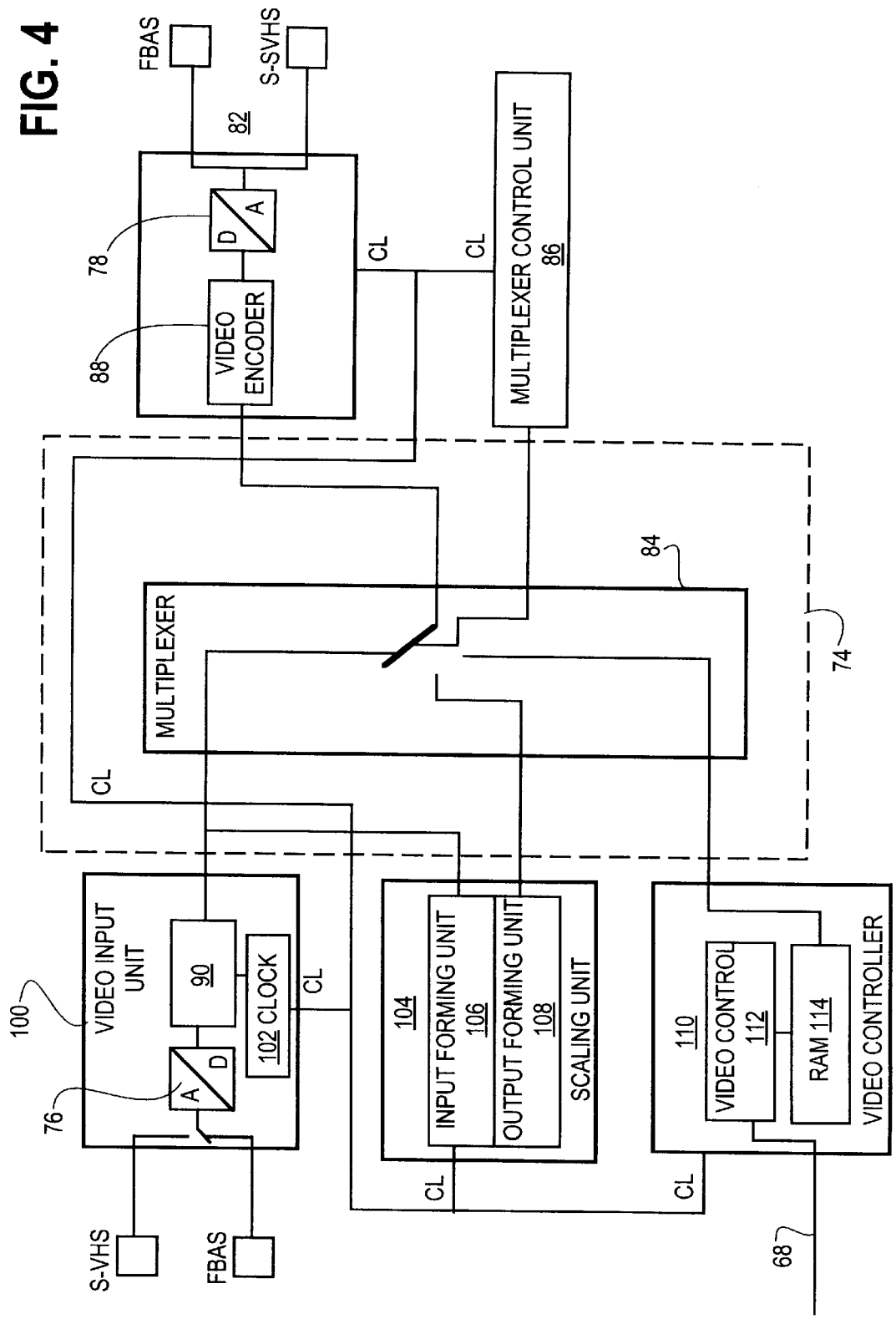
Figure 5:
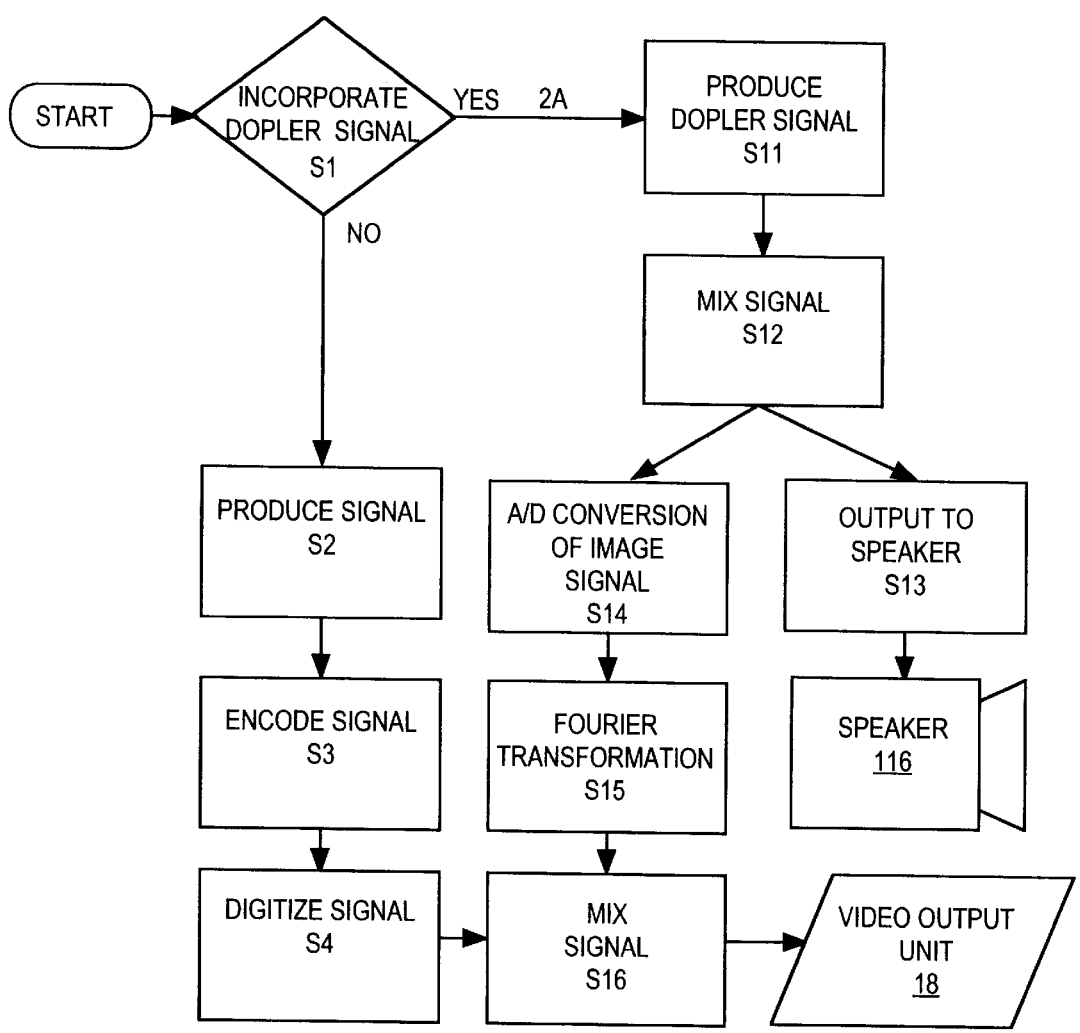

Further advantages, features and details of the invention will be apparent from the following description of embodiments and with reference to the drawings in which:

FIG. 1 is a schematic block circuit diagram of the apparatus according to the invention for viewing blood vessels in body cavities and hollow organs, with the essential functional components, FIG. 2 is a diagrammatic view of a display screen representation by way of example on the video output unit in accordance with a preferred embodiment of the invention (best mode), FIG. 3 shows a block circuit diagram of the Doppler and video unit from FIG. 1, FIG. 4 shows a block circuit diagram in greater detail of the video processing unit from FIG. 3, and FIG. 5 shows a flow chart with the process or procedural steps for producing a combined Doppler and endoscope image representation on the video output unit as shown in FIG. 2.

A commercially available, flexible endoscope 10 is connected in conventional manner to an endoscopy base unit 12 which has the electronics required for endoscope image production. The endoscopy unit 10, 12 which is constructed in that way corresponds to commercially available endoscopy systems, in regard to its component parts and the mode of operation thereof, while—depending on the respective situation of use involved—it is possible to use items of equipment for flexible endoscopy or however for rigid endoscopy, for example in the case of laparoscopy.

In addition a suitably shaped ultrasonic probe 14 provided with a thin flexible supply line is passed to an intervention location at the endoscope end through the instrument or working passage (not shown in the Figures) of the flexible endoscope (endoscope conduit) 10. That ultrasonic probe is adapted to send and receive ultrasonic waves for vessel recognition and observation, making use of the Doppler effect, and is connected by way of a suitable supply line to a Doppler and video unit 16. That Doppler and video unit 16 additionally receives the endoscope image signal (which for example can be the output signal of a device at the end of a video endoscope, which was processed in suitable and otherwise known manner by the base unit 12 to constitute a monitor image) and produces therefrom a common video signal which is outputted to a video output unit 18 in the manner to be described hereinafter. In that respect the common video signal is based both on items of image information which are obtained with the ultrasonic probe 14 and also on the endoscopy image.

A diagrammatically illustrated, externally connected change-over switch—in the illustrated example being a foot switch 20—permits an operator to switch over between modes of image representation on the display unit 18. The arrangement further includes an external interface or remote-operation unit 22 which permits additional external output and processing of the items of information produced by the apparatus according to the invention, and by way of which possible control commands can additionally possibly be provided.

As shown in FIG. 1 by the function module 10, 14 which is diagrammatically indicated in mutually juxtaposed relationship, the combination of a flexible endoscope and an ultrasonic probe which is also flexible is suitable for being guided to the respective positions to be viewed in the body cavity or organ cavity in order there by way of the endoscope to produce a visual image of the respective location being viewed and, by means of the ultrasonic probe—preferably in a multi-channel mode—to permit simultaneous investigation of the (blood) vessels extending at that viewing position.

The examination and representation options and possibilities are illustrated by means of the diagrammatic video image representation in FIG. 2 which shows a typical monitor output image.

In the illustrated embodiment, arranged within a display screen surface in the bottom right region is an area or a window for the actual endoscopy image 26 corresponding to the output signal which is produced by the endoscopy base unit 12. In addition, as the illustrated embodiment involves an 8-channel ultrasonic Doppler unit, the display screen surface 24 presents images of eight ultrasonic representations $28_a$ to $28_h$ which—graduated in terms of their depth of penetration—show blood flow and therefore the presence of a vessel at a respective depth of penetration. More precisely, in the illustrated embodiment, eight ultrasonic depths of penetration are set at between 0.5 and 4.0 mm, as can be seen from the depth displays besides each respective ultrasonic representation, which show a respective processed ultrasonic signal. In the embodiment shown in FIG. 2, with a depth of penetration of 1.0 and 1.5 mm, it is possible to see a Doppler signal with a signal configuration which is pulsed in accordance with heart rate, which indicates that a blood vessel exists in that depthwise region (in relation to the tip of the ultrasonic probe).

The image representation of the ultrasonic Doppler signal in the windows 28 in FIG. 2 is a representation of a respectively ascertained frequency spectrum (vertical axis) in relation to time (horizontal axis), the Doppler reception signal being subjected to subsequent image processing and transformation treatment to produce the illustrated frequency spectrum in relation to time, in an otherwise known fashion, for affording that representation. In addition, the image representation of the windows 28 contains amplitude information, that is to say a representation of a respective signal strength within a frequency line, by an amplitude-dependent colored coloration of the Doppler signal, which is preferably calibrated in dB, as is only indicated in the Figure by means of a color/gray scale 30. In the illustrated configuration, the time lapse on the entire horizontal time axis is about 6 seconds.

Finally, provided on the display screen surface 24 is text area 32 which is suitable for displaying current operating parameters—ultrasonic transmission power, horizontal deflection, gain, wave form and the like.

The image representation on the display screen surface 24 can also be switched over in a simple manner by means of the foot switch 20 between the arrangement shown in FIG. 2 and full-image representation of the endoscopy image 26 so that, for example in the case of endoscopy full image representation, the operator can implement an inspection of the body cavity in question and moves the head of the endoscope until a position which is to be examined more closely is reached. The ultrasonic probe is then put into position in the region which is of interest, whereupon then the arrangement is switched over by the foot switch 20 to the mode of representation shown in FIG. 2 and additional Doppler (vessel) information is directly visually available, for the current position of the endoscope conduit head. That then not only permits direct detection of the position and depth of a blood vessel by means of the stepped, multi-channel Doppler output (this would not be purely optically perceptible through the endoscope as the blood vessels are concealed within a respective organ wall), in addition both the blood flow and also the presence of any foreign or troublesome bodies (for example embolisms) in the blood flow can be immediately optically detected by means of the differently colored amplitudes of a respective frequency portion in the Doppler image. In that respect the frequency color scale 30 permits quantitative evaluation of an object of that kind, which is accentuated in terms of color. The position of the probe can be checked and possibly corrected at any time with the small image portion until a signal has been found or it is certain that there is no vessel present.

Accordingly, the above-described procedure permits investigation, which was hitherto impossible, of indications which are related for example to bleeding out of the gastro-intestinal tract. These are inter alia ulcers, varices, angiodysplasiae or also intervention procedures such as for example polypectomy of large polyps or tumor resection. The result of a combined endoscopy-Doppler investigation of locations of that kind which are subject to the danger of bleeding then permits a decision about further therapeutic measures, for example local therapy, or however a finding that it is not necessary to perform an operation. Any intervention/operation could then be effected in the otherwise known manner directly by way of the working or instrument passage of the endoscope.

The detail structure of the diagrammatic Doppler and video unit 16 shown in FIG. 1 is described hereinafter with reference to FIGS. 3 and 4.

As shown in FIG. 3, it comprises three functional units—a Doppler unit 34 to which the ultrasonic probe 14 can be connected by way of a probe socket 36, a central control unit 38 which receives the prepared output signal from the Doppler unit 34 and subjects it to further processing, and a video processing unit 40 which on the one hand receives a prepared video Doppler signal from the control unit 38 and which on the other hand has signal inputs for the endoscopy image signal which is produced by the endoscopy base unit 12.

More specifically the Doppler unit 34 has a transmission module 42 and a reception module 44 which, by way of the probe 14 connected to both modules, bring a (for example 16 MHz) Doppler ultrasonic signal to the location in the body of interest, or receive the signal that is reflected from there. Suitable clock timing or delay on the reception end (gating) provides in a particularly advantageous manner for the reception of a plurality of reflected signals of a—preferably common—transmission signal which then, due to the transit time differences caused by the time delay, corresponds to a respective depth of penetration. In other words, in the case of the specifically illustrated, eight-channel embodiment by way of example, the ultrasonic signal which is emitted at the transmission end is received by way of the reception module 44 in time-displaced relationship at eight different successive reception times, wherein the time delay between the transmission pulse and the reception of a respective reception signal corresponds to double the signal transit time (out and back) for the respective depth of penetration. That then affords the eight-channel reception signal which, by means of respective mixer units 46 which are each provided in duplicate (in a two-channel configuration), is demodulated in the otherwise known manner or converted to an end frequency which can be subjected to further processing. The demodulated, eight-channel reception signal is then fed to a multiplexer unit 48 which assembles the eight-channel signal for joint, further transmission and processing and makes it available to subsequent function blocks.

At the same time, procedural control and monitoring of the Doppler mode of operation with the above-described units is effected by way of a processor unit 50 or an RAM-control unit 52 co-operating therewith.

The multiplexer unit 48 makes the demodulated Doppler signal available by way of an analog audio signal line 54 and an analog image signal line 56 on the one hand to an audio output unit 58 of the control unit 38 and on the other hand to an A/D-converter unit 60 for subsequent further digital processing of the image signal. Control signals flow by way of a separate control signal line 59.

While the audio output unit 58 is provided for connection to an audio sound transducer (not shown), for example a headset or loud speaker, for output of the demodulated Doppler signal which is converted into the LF-range (individually in channel-wise manner or summed over all channels) (this corresponds to the traditional and still conventional way of using a Doppler ultrasonic unit by a trained operator who can draw diagnostic conclusions from characteristic sounds of the audio unit), the A/D-converter 60 is connected upstream of a signal processor 62 which subjects the digital image signal to mathematical processing. In particular at this location continuous and periodic (fast) Fourier transformation of the respective channel-wise image signals is effected by program control from a program stored in a flash-EPROM 64 or in conjunction with a working store or memory 66 (preferably implemented in the form of an SRAM), in such a way that the signal representations of the respective frequency, which are indicated in FIG. 2 by reference numeral 28, occur as a function of time with a color-accentuated amplitude. In other words, the ultrasonic Doppler signal is converted by means of the Fourier transformation step from the time domain into the frequency domain, the (frequency) spectral lines received at a respective moment in time are calculated and quantified along the path of a respective spectral line in portion-wise manner in view of their signal amplitude for color distinction in accordance with reference scale 30.

The multi-channel Doppler signal produced in that way, which is transformed into the desired form of representation, is then supplied by way of a Doppler image data line 68 to the video processing unit 40. In addition the arrangement has digital (control) signal lines which on the one hand connect the signal processor 62 to the control unit 50 of the Doppler unit 34 and which on the other hand connect the signal processor 62 to the video processing unit 40. By way of those lines, the process steps of the respective function modules involved are controlled and co-ordinated.

In addition the control unit 38 also has the foot switch 20 shown in FIG. 1, illustrated in the form of a diagrammatic function block. Also provided are further operating elements 70 which are possibly required, as well as a serial interface or remote-operation unit 22 and a suitable printer 72 which for example in otherwise known manner can be in the form of an integrated thermal printing module.

In principle, the video processing unit 40 shown in FIG. 3 comprises a central video mixer 74 which operates digitally and which is connected on both sides to suitable A/D- and D/A-converters 76, 78. At the input side the A/D-converter 76 receives the endoscope image signal of the endoscopy base unit 12 by way of a video input port 80 (which can be switched over) and on the output side the D/A-converter 78 outputs the video mixed signal by way of suitably standardised video outputs 82 to a monitor which is to be connected thereto.

Reference will be made hereinafter to the more detailed view in FIG. 4 to describe the mode of operation of the video processing unit 40.

It will be seen here that the central video mixing unit 74 is in the form of a multiplexer 84 which as a reaction to an associated multiplexer control unit 86 switches over or changes between three video signal sources and supplies the resulting signal to the output-side D/A-converter 78, on the input side of which is connected a video encoder 88 for standard image generation (for example PAL, NTSC, SECAM). It is also possible to provide the possibility of processing RGB-signals.

Alternatively or additionally it is possible to process image data in the form of graphic image signals, as correspond for example to current (PC-) graphic standards. Particularly preferably therefore the image-processing components of the invention are graphicable in a suitable fashion.

For treatment of the endoscope video input signal, a suitable video standard decoder 90 is connected in that respect on the output side of the input-side A/D-converter 76; the output signal of the decoder 90 is applied as a first channel to the multiplexer 84.

A further component of the endoscope video input unit 100 is also a system clock generator 102 which applies a common system clock CL to all functional groups of the video processing unit in FIG. 4.

The output signal of the decoder 90 is also received by a video scaling unit 104 which converts the incoming (frame) endoscope image into the intended end format, for example the window representation 26 in FIG. 2. For that purpose the scaling unit 104 has an input formatting unit 106 and an output formatting unit 108. A video controller unit 110 for the digital Doppler image signal coming in from the control unit 38 (for simplification purposes the Doppler image data line 68 is shown combined with the parallel control data line) forms the third input channel for the multiplexer 84, being after the video scaling unit 104 (second channel). As shown, the video controller unit 110 has a control unit 112 co-operating with a video RAM 114.

Now, depending on the preselected mode of representation, the multiplexer 84 switches over between the image input sources or changes between same, so that the intended representations are provided at the output side: either the endoscope image in an entire-image representation or an individual image representation, which is subdivided in window mode, of the individual ultrasonic Doppler channels, mixed in the manner set forth in the foregoing description with a scaled-down endoscopy image. While in the former case the endoscope input image signal is passed directly to the output by way of the multiplexer 84, in the case of the mixed or hybrid representation, that is to say with a reduced endoscopy image plus Doppler representation, the arrangement is switched over with a high cycle number between the corresponding input sources so that the mixed or hybrid signal is then produced at the output side.

The described arrangement then permits the various, examination-relevant items of image information to be simply brought together for direct use by an operator at one glance. In that way it is not only possible for the operating personnel—for example an endoscope operative/operator— to be relieved of the burden of distracting operating steps; in addition, the novel combined image representation for the first time also allows for a procedure in operation which can deal with relatively complex diagnostic and treatment tasks.

A process for operation of the above-described apparatus is described in greater detail with reference to FIG. 5.

After the start of the process, a decision is made as to whether the (multi-channel) Doppler signal is to be incorporated into the intended video image representation (S1). If that is to be affirmed—for example because the foot switch 20 is in a corresponding switching position—then in step S11 the high-frequency Doppler transmission signal is produced (transmission module 42) and radiated by way of the ultrasonic probe 14 connected thereto. The reflected signal is received in a multi-channel mode, corresponding to a respective depth of penetration, and mixed (step S12).

Then, on the one hand, the procedure involves audio signal amplification and output to a loudspeaker unit 116 (step S13), while on the other hand the analog image signal is then converted in multi-channel mode into a digital signal (step S14), subjected to further digital processing and preparation (Fourier transformation) in step S15 and mixed in step S16 with the digitised endoscope signal in the above-described manner.

That endoscopy signal was produced in step S2 by means of the video endoscope, encoded in step S3 and then digitised (S4). The image signal mixed in step S16 is finally outputted to the video output unit 18.

In the situation where only a full-image or frame representation of the endoscope image is wanted (decision in step S1: no), then operation is only implemented along the sequence S2-S3-S4-S16, in which case, during the mixing operation in step S16, a corresponding full-image or frame signal source is switched to the video output unit (see the illustration in FIG. 4). It is also possible in principle to apply the endoscopy image signal to the mixer only when the Doppler apparatus is switched on and otherwise to by-pass the mixer; image quality could be improved thereby, by virtue of separation of the image signals.

In accordance with the invention therefore it is possible to solve the problem which arises out of the state of the art, involving simultaneous monitoring of an endoscope image with checking, that is additionally necessary, for any blood vessels that may be present, so that the operator can direct correspondingly greater attention to the endoscopic investigation. At the same time in accordance with the invention there is accurate and reliable information about the presence and any depth of a blood vessel, while in this respect in particular the embodiment with the eight channels described affords a good information basis.

In that respect, it is possible to preselect or set a respective level of ultrasound power and also further parameters, for example the graduation in respect of the depths of penetration, depending on the desired purpose of use. In accordance with a further development of the invention, it is also provided that a respective predetermined parameter configuration can be called up and set, for example by means of a selection menu in respect of the most important indications.

If for example in the case of ulcer inspection for a potential ulcer in the stomach or intestine an endoscopic examination is to be effected, a depth of penetration which is graduated in 0.3 mm, in respect of the eight reception channels, at between about 0.3 and about 2.4 mm, is set, being suitable for detecting possible blood vessels. The horizontal time axis in regard to representation of the ultrasonic Doppler signals at 6 seconds is sufficient for 4 to 6 cardiac cycles; it will be appreciated that in this case also a setting is to be implemented according to the situation involved, in accordance with the wishes of the operator (or the relevant expert).

The present invention is not restricted to use with eight ultrasonic Doppler channels—on the contrary it is also possible here to use any number of channels required, depending on the intended purpose of use, for example about between 1 and 16, and also the described image representation and arrangement in FIG. 2 is to be interpreted as having been given purely by way of example. Admittedly, in terms of practical operation, it has proven to be worthwhile, from the point of view of an operator, to substantially limit the possibility of manually influencing the arrangement on the display screen in order to avoid involving here an additional potential distraction; nonetheless it is a matter for the discretion of the average man skilled in the art to design or technically implement any image and window arrangements on the display screen as he wishes. That would also include selective (accentuating) enlargement of individual Doppler representations. In principle acoustic output of the Doppler signal could also be permanently effected.

The choice of a suitable Doppler probe also depends on the options afforded by an available endoscope. Thus it has been found in practice that endoscopic Doppler probes of that kind, with their feed lines and conduits, should not exceed an outside diameter of 2.6 mm (for flexible endoscopy) for insertion into the corresponding instrument passage. Here too however the configuration involved can be adapted to the respective requirements concerned.

In accordance with the invention a development thereof provides for effecting accurate placement or adjustment of the Doppler probe position on site: it projects a certain distance out of the instrument passage and by suitable manipulation operations, for example an additionally induced movement of the probe head, can be positioned in relation to the surrounding organ walls. It is precisely in view of the fact that Doppler sonographic detection is particularly effective with a probe position substantially tangentially relative to a vessel to be viewed that this technology in accordance with a development of the invention also affords considerable potential for improvement and optimisation.

Besides such a probe movement which could be effected mechanically for example in the manner of a known controllable catheter, it would be possible to use a rotating probe or however to provide for electrical or lens-technology influencing of the probe detection region (or its sound field) by suitable circuitry measures.

The present invention is not limited to the above-described embodiment involving the use of an endoscope in connection with ultrasonic detection of body vessels.

Thus there is in particular also a suitable embodiment (not shown in the Figures) for using the invention in connection with microscopes or the like instruments, the image of which is detected by an image detection sensor—for example a CCD-element—and used for further processing along the lines of image mixing in accordance with the invention. That would afford for example the possibility of using such a video microscope in neurosurgery in such a way that a microscope is placed in front of the area of operation and the operator looks through it. The microscope image which is detected by the CCD-sensor is then represented on a monitor by way of a suitable video image preparation procedure, optionally for mixing with an ultrasonic Doppler signal which is produced by an ultrasonic probe. That ultrasonic probe can either be carried on the image detection element or the associated carrier (in this case: the microscope) or it can be separate therefrom, for example by means of a hand-held carrier.

What is claimed is:

1. An apparatus for viewing blood vessels, on the body, in body openings, cavities, and hollow organs, the apparatus comprising:
   an image detection element held on a carrier device which is guided into a viewing position, and an ultrasonic transducer which is provided at the intervention end on the carrier device,
   an ultrasonic unit connected to the ultrasonic transducer and which is designed to detect an organ and/or fluid movement at least one predetermined spacing from the ultrasonic transducer,
   an evaluation unit which is connected to the ultrasonic unit and which is designed for digital conversion of an output signal of the ultrasonic unit into an output image signal which visually represents the organ and/or fluid movement at the at least one predetermined spacing,
   a video output unit which receives the output image signal of the evaluation unit and an electronic image signal of the image detection element and which is designed to produced a combined overall image for a display screen which is able to display both a detected image and also at least one representation of the organ and/or fluid movement, and
   a mode selection device which acts on operation of the video output unit and which is adapted for switching over from a first mode of operation with a detected full image of the image detection element, in particular an endoscopy full image, into a second mode of operation with the combined overall image on the display screen.

2. An apparatus as set forth in claim 1 characterised in that the carrier device with the image detection element is an endoscope.

3. An apparatus as set forth in claim 1 characterised in that the carrier device is in the form of an operational microscope and the ultrasonic transducer is provided separately therefrom.

4. An apparatus as set forth in claim 1 characterised in that the fluid movement is a movement of blood in the blood vessel.

5. An apparatus as set forth in claim 1 characterised in that the ultrasonic transducer is adapted to be guided in a working or instrument passage of an endoscope into an operative position at the end.

6. An apparatus as set forth in claim 1 characterised in that the ultrasonic unit is adapted to detect the organ and/or fluid movement at a plurality of spacings corresponding to various depths of penetration.

7. As apparatus as set forth in claim 6 characterised in that the ultrasonic unit has a controllable delay device which determines the plurality of depths of penetration on the basis of a respective signal transit time.

8. An apparatus as set forth in claim 1 characterised in that a plurality of movement representations is shown on the overall image, corresponding to a detected plurality of predetermined spacings relative to the ultrasonic transducer.

9. An apparatus as set forth in claim 8 characterised in that the plurality of movement representations is arranged window-like and in a succession in respect of respective depths of penetration.

10. An apparatus as set forth in claim 1 characterised in that the mode selection device is in the form of a remote-operation unit, including a foot switch.

11. An apparatus as set forth in claim 1 characterised in that the video output unit has a digital video mixing device.

12. An apparatus as set forth in claim 1 characterised in that the video output unit has a digital scaling unit for the detected image of the image detection element.

13. An apparatus as set forth in claim 1 characterised by a decoder and/or encoder for TV-picture signals, including PAL, NTSC, and SECAM.

14. An apparatus as set forth in claim 1 characterised in that the ultrasonic transducer is a component part of a probe device which has a mechanical positioning device for altering a position of the ultrasonic transducer at the viewing position.

15. An apparatus as set forth in claim 1 characterised in that the ultrasonic transducer is provided with a device for the controlled electronic change in the transducer sound field.

16. A process for viewing blood vessels, comprising the following steps:

fitting or introducing a transducer to a viewing position in a body cavity, in a hollow organ or to a body by means of a carrier device having an image detection element and an ultrasonic unit, producing ultrasonic signals reflected at a vessel at the viewing position, converting the signals into a visual representation of a fluid movement in the vessel, producing a combined monitor-overall image from the representation of the fluid movement and an image produced by the image detection element on a monitor device, and producing a full image of the image detection element on the monitor device upon actuatation of a mode selection device.

17. A process as set forth in claim 16 characterised by the following steps:

producing a plurality of representations of the fluid movement for a corresponding plurality of depths of penetration relative to the ultrasonic transducer, and simultaneously incorporating the plurality of representations into the combined monitor-overall image.

* * * * *